United States Patent [19]

Sugiyama et al.

[11] Patent Number: 4,590,198

[45] Date of Patent: May 20, 1986

[54] FUNGICIDAL ISONICOTINANLLIDE RETALS, THEIR COMPOSITIONS AND METHOD OF USING THEM

[75] Inventors: Hiroshi Sugiyama, Tokyo; Keizo Hosoda, Shizuoka; Masanori Okada, Saitama; Yoshitaka Iwane, Kanagawa; Yasushi Murakami, Tokyo, all of Japan

[73] Assignee: Chugai Seiyaku Kabushiki Kaisha, Tokyo, Japan

[21] Appl. No.: 578,048

[22] Filed: Feb. 7, 1984

[30] Foreign Application Priority Data

Feb. 24, 1983 [JP] Japan .................................. 58-29929
Apr. 28, 1983 [JP] Japan .................................. 58-73865
Sep. 30, 1983 [JP] Japan .................................. 58-180774

[51] Int. Cl.$^4$ .................... A61K 31/455; C07D 213/81
[52] U.S. Cl. ..................... 514/336; 514/354; 546/268; 546/283; 546/323
[58] Field of Search ....................... 546/283, 323, 268; 424/266; 514/336, 354

[56] References Cited

U.S. PATENT DOCUMENTS

| | | | |
|---|---|---|---|
| 4,147,793 | 4/1979 | Shephard et al. | 424/273 R |
| 4,244,730 | 1/1981 | Kobzina | 564/212 |
| 4,377,407 | 3/1983 | Shirakawa et al. | 546/323 |
| 4,435,202 | 3/1984 | Koizumi et al. | 546/323 |

FOREIGN PATENT DOCUMENTS

| | | | |
|---|---|---|---|
| 0048998 | 4/1982 | European Pat. Off. | |
| 53-72825 | 6/1978 | Japan . | |
| 1494695 | 12/1977 | United Kingdom . | |
| 2047701 | 12/1980 | United Kingdom | 71/76 |

OTHER PUBLICATIONS

Chemical Abstracts, 91:85064a (1979).

Primary Examiner—Jane T. Fan
Attorney, Agent, or Firm—Browdy and Neimark

[57] ABSTRACT

Novel acetal compounds of the formula:

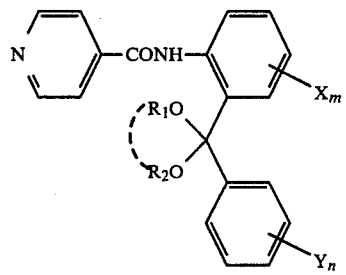

wherein X is a halogen atom, a trifluromethyl group or a lower alkyl group; Y is a halogen atom, a lower alkyl group or a lower alkyloxy group; m and n each independently are an integer of 0 to 2, and when m or n is 2, the plurality of each of X or Y may have the same or different meanings; $R_1$ and $R_2$ independently represent a saturated or unsaturated lower hydrocarbon residue, or $R_1$ and $R_2$ together form a substituted or unsubstituted alkylene chain which, when taken together with

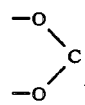

to which they are attached, form a ring structure, and a process for their production are provided. The compounds are highly effective against pathogenic fungi while being well tolerated by cultivated plants.

22 Claims, No Drawings

FUNGICIDAL ISONICOTINANLLIDE RETALS, THEIR COMPOSITIONS AND METHOD OF USING THEM

BACKGROUND OF THE INVENTION

Description of the Prior Art

Many synthetic organic compounds and antibiotics have been found to have the ability to kill fungi and several of them have been commercialized for use as agricultural and horticultural fungicides. However, two big problems have arisen that require early solution: one is that some fungi have acquired resistance to these compounds, and the other problem is that these fungicides will cause environmental pollution if they are used in large quantities.

The present invention is the result of our extensive studies to develop a compound that has a novel basic structure and exhibits high efficacy even if it is used in a small amount as an effective ingredient.

SUMMARY OF THE INVENTION

One object of the present invention is to provide a novel ketal compound which is highly effective against pathogenic fungi while having little toxic effect on cultivated plants, and a process for producing said compound.

Another object of the present invention is to provide a method for controlling pathogenic fungi on plants or in soil by use of said compound.

Further objects will become clear from the following descriptions.

DETAILED DESCRIPTION OF THE INVENTION

The present invention relates to ketal compounds of formula (I):

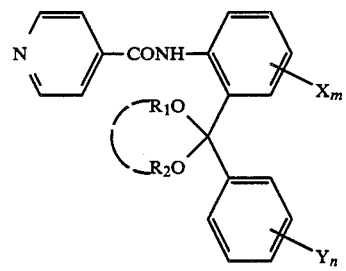
(I)

wherein X is a halogen atom, a trifluoromethyl group or a lower alkyl group; Y is a halogen atom, a lower alkyl group or a lower alkyloxy group; m and n each independently are an integer of 0 to 2, and when m or n is 2, the plurality of each of X or Y may have the same or different meanings; $R_1$ and $R_2$ independently represent a saturated or unsaturated lower hydrocarbon residue, or $R_1$ and $R_2$ together form a substituted or unsubstituted alkylene chain such as

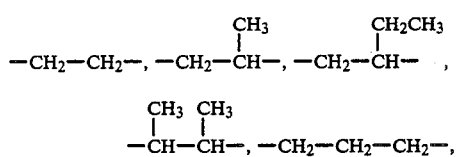

which alkylene chain forms a cyclic structure including

to which they are attached. The present invention also relates to a process for producing such ketal compounds, and an agricultural and horticultural fungicide containing one or more of these ketal compounds as an effective ingredient.

The compound of formula (I) is novel and exhibits high efficacy against diseases affecting cultivated plants. However, this compound is by no means toxic to humans, animals and fish, and causes no adverse effects on cultivated plants.

The compound of formula (I) used in a horticultural fungicide has both preventive and curative effects against a wide spectrum of pathogenic fungi such as Phycomycetes, Ascomycetes, Basidiomycetes and Deuteromycetes. The compound is particularly efficacious against powdery mildew, rust diseases, downy mildew and seedling damping-off which affect cultivated plants.

The production of the compound of formula (I) starts with a known benzophenone derivative (II) (see, for example, Japanese Patent Laid Open Public No. 139306/80):

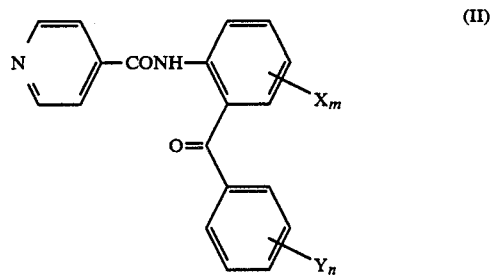
(II)

wherein X, Y, m and n have the same meanings as defined above. This starting material is reacted with a suitable halogenating agent such as thionyl chloride, thionyl bromide or phosphorus pentachloride in the absence or presence of an inert solvent such as methylene chloride, chloroform, benzene, toluene, tetrahydrofuran, diisopropyl ether or dioxane. The resulting reaction product is then reacted with a corresponding alcohol. By this procedure, the desired compound (I) can be easily obtained in high yield. The reaction with the corresponding alcohol can be carried out smoothly by using a suitable acid acceptor such as triethylamine, pyridine, N,N-dialkylaniline, sodium hydroxide, potassium hydroxide or sodium alkoxide. In this second reaction, an inert solvent as mentioned above may be used.

Some of the compounds of formula (I) thus prepared have asymmetric carbon atoms in their structure, and obviously, they are obtained as different optical stereoisomers. More specifically, if $R_1$ and $R_2$ combine to form a cyclic structure, namely the dioxolane structure having a substituent such as an alkyl group at 4-position, the carbons at 4- and 2-position are respectively asymmetric.

The optical stereoisomers of compound (I) can be resolved and isolated by a suitable known technique. These optical isomers are also included in the scope of the present invention.

The production of compounds of formula (I) is illustrated by the following examples of synthesis.

SYNTHESIS 1

2-(4-Chlorobenzoyl)-isonicotinanilide diethyl ketal (Compound No. 9)

2-(4-Chlorobenzoyl)-isonicotinanilide (11 g) was added to thionyl chloride (100 ml) and the mixture was heated for 4 hours under reflux. Under reduced pressure, the thionyl chloride was distilled off completely. To the resulting reaction product, ethyl alcohol (100 ml) was added under cooling with ice, and triethylamine (15 ml) was slowly added dropwise. After the completion of the addition, the mixture was stirred for another 2 hours at room temperature. After distilling off under vacuum, water was added and the mixture was extracted with ethyl acetate. The resulting ethyl acetate layer was dried over magnesium sulfate and the ethyl acetate was distilled off under vacuum. Upon recrystallizing the residue from a mixed solvent of ethyl acetate and n-hexane, the titled compound was obtained in an amount of 11.0 g (yield: 80%). m.p. 98°–99° C.

Analysis: Calcd. for $C_{23}H_{23}ClN_2O_3$ (m.w. 410.89): C 67.23, H 5.64, N 6.82 (%). Found: C 67.09, H 5.72, N 6.70 (%).

SYNTHESIS 2

2-(4-Chlorobenzoyl)-isonicotinanilide dimethyl ketal (Compound No. 4)

The procedure of Synthesis 1 was repeated except that ethyl alcohol was replaced by methyl alcohol. The titled compound was obtained in an amount of 10.2 g (yield: 80%). m.p. 137°–138° C.

Analysis: Calcd. for $C_{21}H_{19}ClN_2O_3$ (m.w. 382.24): C 65.99, H 5.01, N 7.33 (%). Found: C 66.05, H 5.08, N 7.23 (%).

SYNTHESIS 3

2-(4-Chlorobenzoyl)-isonicotinanilide di-n-propyl ketal (Compound No. 42)

The procedure of Synthesis 1 was repeated except that ethyl alcohol was replaced by n-propyl alcohol. The titled compound was obtained in an amount of 12.4 g (yield: 85%). m.p. 140°–141° C.

Analysis: Calcd. for $C_{25}H_{27}ClN_2O_3$ (m.w. 438.95): C 68.41, H 6.20, N 6.38 (%). Found: C 68.28, H 6.24, N 6.31 (%).

SYNTHESIS 4

2-(4-Chlorobenzoyl)-isonicotinanilide di-n-butyl ketal (Compound No. 41)

The procedure of Synthesis 1 was repeated except that ethyl alcohol was replaced by n-butyl alcohol. The resulting product was purified by column chromatography on silica gel, and the titled compound was obtained as an oily product in an amount of 12.5 g (yield: 80%). The NMR data for this compound is shown in the footnotes to Table 1.

Analysis: Calcd. for $C_{27}H_{31}ClN_2O_3$ (m.w. 467.00): C 69.44, H 6.69, N 6.00 (%). Found: C 69.35, H 6.74, N 5.89 (%).

SYNTHESIS 5

2-(4-Methylbenzoyl)-isonicotinanilide diethyl ketal (Compound No. 25)

The procedure of Synthesis 1 was repeated except that 2-(4-chlorobenzoyl)-isonicotinanilide was replaced by 2-(4-methylbenzoyl)-isonicotinanilide (10.5 g). The titled compound was obtained in an amount of 11.7 g (yield: 90%). m.p. 95°–96° C.

Analysis: Calcd. for $C_{24}H_{26}N_2O_3$ (m.w. 390.48): C 73.82, H 6.71, N 7.17 (%). Found: C 73.77, H 6.78, N 7.21 (%).

SYNTHESIS 6

2-(4-Methylbenzoyl)-isonicotinanilide di-n-propyl ketal (Compound No. 33)

The procedure of Synthesis 5 was repeated except that ethyl alcohol was replaced by n-propyl alcohol. The titled compound was obtained in an amount of 11.9 g (yield: 85%). m.p. 120°–121° C.

Analysis: Calcd. for $C_{26}H_{30}N_2O_3$ (m.w. 418.54): C 74.61, H 7.23, N 6.69 (%). Found: C 74.47, H 7.30, N 6.61 (%).

SYNTHESIS 7

4-Chloro-2-benzoyl-isonicotinanilide diethyl ketal (Compound No. 7)

The procedure of Synthesis 1 was repeated except that 2-(4-chlorobenzoyl)-isonicotinanilide and triethylamine was replaced by 4-chloro-2-benzoyl-isonicotinanilide (11.2 g) and N,N-diethylaniline (15 ml), respectively. The titled compound was obtained in an amount of 10.3 g (yield: 75%). m.p. 133°–134° C.

Analysis: Calcd. for $C_{23}H_{23}ClN_2O_3$ (m.w. 410.89): C 67.23, H 5.64, N 6.82 (%). Found: C 67.35, H 5.59, N 6.91 (%)

SYNTHESIS 8

4-Chloro-2-(4-chlorobenzoyl)-isonicotinanilide diethyl acetal (Compound No. 13)

4-Chloro-2-(4-chlorobenzoyl)-isonicotinanilide (12.4 g) was reacted as in Synthesis 1 using pyridine (10 ml) instead of triethylamine. The titled compound was obtained in an amount of 11.1 g (yield: 75%). m.p. 123°–124° C.

Analysis: Calcd. for $C_{23}H_{22}Cl_2N_2O_3$ (m.w. 445.34): C 62.03, H 4.98, N 6.29 (%). Found: C 59.97, H 5.07, N 6.24 (%).

SYNTHESIS 9

2-Benzoyl-isonicotinanilide dimethyl acetal (Compound No. 1)

2-Benzoyl-isonicotinanilide (10 g) was added to benzene (200 ml) and the mixture was heated at the reflux temperature under stirring. Thionyl chloride (20 ml) was gradually added to the mixture which was heated for 4 hours under stirring. After cooling to room temperature, the benzene and excess thionyl chloride were completely distilled off under vacuum. The resulting residue was gradually added under stirring to a solution of sodium hydroxide (3 g) in methyl alcohol (100 ml) and the mixture was stirred for another 2 hours at room temperature. After distilling off the methyl alcohol under vacuum, water was added and the mixture was extracted with ethyl acetate. The ethyl acetate layer was separated and dried over anhydrous sodium sulfate. The ethyl acetate was distilled off under vacuum. Upon recrystallization from a mixed solvent of ethyl acetate and n-hexane, the titled compound was obtained in an amount of 7.5 g (yield: 65%). m.p. 123°–124° C.

Analysis: Calcd. for $C_{21}H_{20}N_2O_3$ (m.w. 348.40): C 72.40, H 5.79, N 8.04 (%). Found: C 72.50, H 5.70, N 8.11 (%).

SYNTHESIS 10

2-Benzoyl-isonicotinanilide diethyl ketal (Compound No. 6)

The procedure of Synthesis 9 was repeated except that methyl alcohol and sodium hydroxide were respectively replaced by ethyl alcohol and 4 g of potassium hydroxide. The titled compound was obtained in an amount of 8.89 g (yield: 70%). m.p. 114°–115° C.

Analysis: Calcd. for $C_{23}H_{24}N_2O_3$ (m.w. 376.45): C 73.38, H 6.43, N 7.44 (%). Found: C 73.30, H 6.51, N 7.39 (%).

SYNTHESIS 11

2-(4-Chlorobenzoyl)-4-fluoro-isonicotinanilide diethyl ketal (Compound No. 16)

To a mixture of phosphorus pentachloride (7.3 g) in benzene (250 ml), 2-(4-chlorobenzoyl)-4-fluoro-isonicotinanilide (12 g) was added, and the mixture was refluxed for 2 hours under stirring. After cooling, the solvent was completely distilled off under vacuum. The resulting residue was gradually added to an ethyl alcohol solution of potassium hydroxide (3.7 g) and allowed to react at room temperature over a period of 2 hours. After completion of the reaction, ethyl alcohol was distilled off under vacuum. The resulting residue was extracted, after addition of water, with ethyl acetate. The ethyl acetate layer was dried over anhydrous sodium sulfate. Thereafter, the ethyl acetate was distilled off under vacuum. Upon recrystallizing the resulting residue with a mixed solvent of ethyl acetate and n-hexane, the titled compound was obtained in an amount of 10.7 g (yield: 75%). m.p. 96°–97° C.

Analysis: Calcd. for $C_{23}H_{22}ClFN_2O_3$ (m.w. 428.71): C 64.44, H 5.13, N 6.53 (%). Found: C 64.27, H 5.00, N 6.61 (%).

SYNTHESIS 12

2-(3,4-Dichlorobenzoyl)-isonicotinanilide diethyl acetal (Compound No. 20)

2-(3,4-Dichlorobenzoyl)-isonicotinanilide (12.4 g) was reacted as in Synthesis 11 except that potassium hydroxide was replaced by metallic sodium (2.0 g). The titled compound was obtained in an amount of 11.9 g (yield: 80%). m.p. 113°–114° C.

Analysis: Calcd. for $C_{23}H_{22}Cl_2N_2O_3$ (m.w. 445.34): C 62.03, H 4.98, N 6.29 (%). Found: C 59.90, H 5.05, N 6.34 (%).

SYNTHESIS 13

4-Bromo-2-benzoyl-isonicotinanilide dimethyl ketal (Compound No. 3)

4-Bromo-2-benzoyl-isonicotinanilide (12.7 g) was treated as in Synthesis 11 except that ethyl alcohol was replaced by methyl alcohol and potassium hydroxide by sodium hydroxide (3 g). The titled compound was obtained in an amount of 11.4 g (yield: 80%). m.p. 189°–190° C.

Analysis: Calcd. for $C_{21}H_{19}BrN_2O_3$ (m.w. 427.29): C 59.03, H 4.48, N 6.56 (%). Found: C 59.11, H 4.56, N 6.64 (%).

SYNTHESIS 14

4-Chloro-2-(4-chlorobenzoyl)-6-methyl-isonicotinanilide diethyl ketal (Compound No. 59)

4-Chloro-2-(4-chlorobenzoyl)-6-methyl-isonicotinanilide (12.8 g) was treated as in Synthesis 1. The titled compound was obtained in an amount of 13.0 g (yield: 85%). m.p. 134°–135° C.

Analysis: Calcd. for $C_{24}H_{24}Cl_2N_2O_3$ (m.w. 459.37): C 62.75, H 5.27, N 6.10 (%). Found: C 62.61, H 5.34, N 5.94 (%).

SYNTHESIS 15

5-Chloro-2-(4-chlorobenzoyl)-6-methyl-isonicotinanilide diethyl ketal (Compound No. 66)

5-Chloro-2-(4-chlorobenzoyl)-6-methyl-isonicotinanilide (12.8 g) was treated as in Synthesis 1. The titled compound was obtained in an amount of 12.2 g (yield: 80%). m.p. 156°–157° C.

Analysis: Calcd. for $C_{24}H_{24}Cl_2N_2O_3$ (m.w. 459.37): C 74.61, H 7.23, N 6.69 (%). Found: C 74.49, H 7.31, N 6.60 (%).

SYNTHESIS 16

2-(4-Chlorobenzoyl)-isonicotinanilide ethylene ketal (Compound No. 73)

2-(4-Chlorobenzoyl)-isonicotinanilide (11 g) was reacted with thionyl chloride as in Synthesis 1. To the resulting product, tetrahydrofuran (150 ml) and ethylene glycol (30 ml) were added and the mixture was stirred for about 20 minutes under cooling with ice. To the resulting solution, triethylamine (25 ml) was added dropwise. After completion of the addition, the solution was stirred for 1 hour, followed by stirring at room temperature for another 4 hours. The resulting solution was treated as in Synthesis 1 to produce the titled compound in an amount of 10.2 g (yield: 80%). m.p. 102°–103° C.

Analysis: Calcd. for $C_{21}H_{17}ClN_2O_3$ (m.w. 380.82): C 66.23, H 4.50, N 7.36 (%). Found: C 66.28, H 4.61, N 7.27 (%).

SYNTHESIS 17

2-(4-Chlorobenzoyl)-isonicotinanilide propylene ketal (Compound No. 76)

2-(4-Chlorobenzoyl)-isonicotinanilide (11 g) was treated as in Synthesis 16 except that ethylene glycol was replaced by propylene glycol. The titled compound was obtained in an amount of 10.5 g (yield: 80%). m.p. 125°–126° C.

Analysis: Calcd. for $C_{22}H_{19}ClN_2O_3$ (m.w. 394.85): C 66.92, H 4.85, N 7.09 (%). Found: C 67.04, H 4.81, N 7.15 (%).

Several other compounds of formula (I) were prepared in a like manner, and they are identified in Table 1. It should be understood that the present invention is by no means limited to the compounds shown in Table 1. The identification numbers of the compounds listed in Table 1 shall apply to the examples of compound synthesis, experiments and preparation of fungicide formulations.

The respective numbers used in Table 1 to indicate the positions of substituents X and Y have the following definitions:

The respective symbols appearing in the column "$R_1$, $R_2$" in Table 1 have the following definitions: Me=methyl, Et=ethyl, Pr=n-propyl, Pr(i)=iso-propyl, Bu=n-butyl, Bu(i)=iso-butyl and All=allyl.

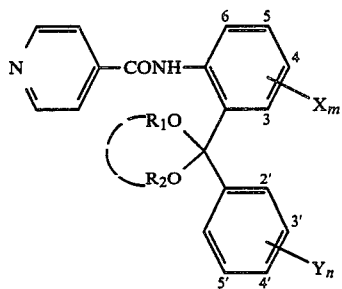

TABLE 1

| Compound No. | X 3 | 4 | 5 | 6 | m | Y 2' | 3' | 4' | 5' | n | $R_1$ $R_2$ | m.p. (°C.) |
|---|---|---|---|---|---|---|---|---|---|---|---|---|
| 1 | H | H | H | H | 0 | H | H | H | H | 0 | Me | 123–124 |
| 2 | H | Cl | H | H | 1 | H | H | H | H | 0 | Me | 170–171 |
| 3 | H | Br | H | H | 1 | H | H | H | H | 0 | Me | 189–190 |
| 4 | H | H | H | H | 0 | H | H | Cl | H | 1 | Me | 137–138 |
| 5 | H | Cl | H | H | 1 | H | H | Cl | H | 1 | Me | (*1) |
| 6 | H | H | H | H | 0 | H | H | H | H | 0 | Et | 114–115 |
| 7 | H | Cl | H | H | 1 | H | H | H | H | 0 | Et | 133–134 |
| 8 | H | Br | H | H | 1 | H | H | H | H | 0 | Et | 135–136 |
| 9 | H | H | H | H | 0 | H | H | Cl | H | 1 | Et | 98–99 |
| 10 | H | H | H | H | 0 | F | H | H | H | 1 | Et | 135–136 |
| 11 | H | Cl | H | H | 1 | Cl | H | H | H | 1 | Et | 127–128 |
| 12 | H | Cl | H | H | 1 | H | Cl | H | H | 1 | Et | 129–130 |
| 13 | H | Cl | H | H | 1 | H | H | Cl | H | 1 | Et | 123–124 |
| 14 | H | Cl | H | H | 1 | H | H | F | H | 1 | Et | 133–134 |
| 15 | H | Cl | H | H | 1 | H | H | Br | H | 1 | Et | 132–133 |
| 16 | H | F | H | H | 1 | H | H | Cl | H | 1 | Et | 96–97 |
| 17 | H | Br | H | H | 1 | H | H | Cl | H | 1 | Et | 154–155 |
| 18 | H | H | H | H | 0 | Cl | H | Cl | H | 2 | Et | 125–126 |
| 19 | H | Cl | H | H | 1 | H | Cl | H | Cl | 2 | Et | 161–163 |
| 20 | H | Cl | H | H | 1 | H | Cl | Cl | H | 2 | Et | 113–114 |
| 21 | H | F | H | H | 1 | H | H | Cl | H | 1 | Me | (*2) |
| 22 | H | H | H | H | 0 | H | H | F | H | 1 | Et | (*3) |
| 23 | H | H | H | H | 0 | H | H | Br | H | 1 | Et | 128–129 |
| 24 | H | H | H | H | 0 | H | Cl | H | H | 1 | Et | (*4) |
| 25 | H | H | H | H | 0 | H | H | CH$_3$ | H | 1 | Et | 95–96 |
| 26 | H | H | H | H | 0 | H | H | H | H | 0 | Pr | 102–103 |
| 27 | H | Cl | H | H | 1 | H | H | Cl | H | 1 | Pr | 96–97 |
| 28 | H | Cl | H | H | 1 | H | H | F | H | 1 | Pr | 85–86 |
| 29 | H | Cl | H | H | 1 | H | H | Br | H | 1 | Pr | 119–120 |
| 30 | H | F | H | H | 1 | H | H | Cl | H | 1 | Pr | 137–138 |
| 31 | H | Br | H | H | 1 | H | H | Cl | H | 1 | Pr | 103–104 |
| 32 | H | H | H | H | 0 | Cl | H | Cl | H | 2 | Pr | (*5) |
| 33 | H | H | H | H | 0 | H | H | CH$_3$ | H | 1 | Pr | 120–121 |
| 34 | H | H | H | H | 0 | H | H | H | H | 0 | Bu | 96–97 |
| 35 | H | Cl | H | H | 1 | H | H | Cl | H | 1 | Bu | 108–109 |
| 36 | H | F | H | H | 1 | H | H | Cl | H | 1 | Bu | 102–103 |
| 37 | H | Br | H | H | 1 | H | H | Cl | H | 1 | Bu | 114–115 |
| 38 | H | CH$_3$ | H | H | 1 | H | H | H | H | 0 | Et | 112–113 |
| 39 | H | CH$_3$ | H | H | 1 | H | H | H | H | 0 | Pr | 89–90 |
| 40 | H | H | H | H | 0 | H | H | CH$_3$ | H | 1 | Me | (*6) |
| 41 | H | H | H | H | 0 | H | H | Cl | H | 1 | Bu | (*7) |
| 42 | H | H | H | H | 0 | H | H | Cl | H | 1 | Pr | 140–141 |
| 43 | H | H | H | H | 0 | H | H | Br | H | 1 | Me | 129–130 |
| 44 | H | H | H | H | 0 | H | H | Br | H | 1 | Pr | 146–147 |
| 45 | H | Cl | H | H | 1 | H | H | CH$_3$ | H | 1 | Pr | (*8) |
| 46 | H | CH$_3$ | H | H | 1 | H | H | Cl | H | 1 | Et | 136–137 |
| 47 | H | Cl | H | H | 1 | H | H | CH$_3$ | H | 1 | Et | 130–131 |
| 48 | H | H | CF$_3$ | H | 1 | H | H | H | H | 0 | Et | 117–118 |
| 49 | H | H | H | H | 0 | H | H | Et | H | 1 | Et | (*9) |
| 50 | H | H | Cl | CH$_3$ | 2 | H | H | H | H | 0 | Et | 168–169 |
| 51 | H | CH$_3$ | H | H | 1 | H | H | Cl | H | 1 | Pr | 82–83 |
| 52 | H | H | CH$_3$ | H | 1 | H | H | Cl | H | 1 | Et | 122–123 |
| 53 | H | H | H | CH$_3$ | 1 | H | H | Cl | H | 1 | Me | 153–154 |
| 54 | H | H | H | CH$_3$ | 1 | H | H | Cl | H | 1 | Et | 56–57 |
| 55 | H | H | H | CH$_3$ | 1 | H | H | Cl | H | 1 | Pr | (*10) |
| 56 | H | CH$_3$ | H | Cl | 2 | H | H | Cl | H | 1 | Me | 161–162 |
| 57 | H | CH$_3$ | H | Cl | 2 | H | H | Cl | H | 1 | Et | 156–157 |
| 58 | H | CH$_3$ | H | Cl | 2 | H | H | Cl | H | 1 | Pr | 158–159 |
| 59 | H | Cl | H | CH$_3$ | 2 | H | H | Cl | H | 1 | Et | 134–135 |

TABLE 1-continued

| | | | | | | | | | | | | |
|---|---|---|---|---|---|---|---|---|---|---|---|---|
| 60 | H | CH₃ | H | Cl | 2 | H | H | Cl | H | 1 | Et | 225–227 |
| 61 | H | CH₃ | H | CH₃ | 2 | H | H | Cl | H | 1 | Et | 229–232 |
| 62 | H | H | Cl | Cl | 2 | H | H | Cl | H | 1 | Me | 187–188 |
| 63 | H | H | Cl | Cl | 2 | H | H | Cl | H | 1 | Et | 147–148 |
| 64 | H | H | Cl | Cl | 2 | H | H | Cl | H | 1 | Pr | 160–161 |
| 65 | H | H | Cl | CH₃ | 2 | H | H | Cl | H | 1 | Me | 190–191 |
| 66 | H | H | Cl | CH₃ | 2 | H | H | Cl | H | 1 | Et | 156–157 |
| 67 | H | H | Cl | CH₃ | 2 | H | H | Cl | H | 1 | Pr | 174–175 |
| 68 | H | H | Cl | CH₃ | 2 | H | H | Br | H | 1 | Et | 148–150 |
| 69 | H | H | Cl | CH₃ | 2 | H | H | Br | H | 1 | Pr | 168–169 |
| 70 | Cl | H | H | CH₃ | 2 | H | H | Cl | H | 1 | Me | 147–148 |
| 71 | H | H | H | H | 0 | H | H | Cl | H | 1 | All | 123–124 |
| 72 | H | Cl | H | H | 1 | H | H | OCH₃ | H | 1 | Et | 167–168 |
| 73 | H | H | H | H | 0 | H | H | Cl | H | 1 | —CH₂—CH₂— | 102–103 |
| 74 | H | H | H | H | 0 | H | H | Cl | H | 1 | —CH₂—CH(CH₃)— | 111–112 |
| 75 | H | H | H | H | 0 | H | H | Cl | H | 1 | —CH₂—CH(CH₂CH₃)— | (*11) |
| 76 | H | H | H | H | 0 | H | H | Cl | H | 1 | —CH₂—CH₂—CH₂— | 125–126 |
| 77 | H | H | H | H | 0 | H | H | Cl | H | 1 | —CH₂CH₂—CH(CH₃)— | 95–96 |
| 78 | H | H | H | H | 0 | H | H | Cl | H | 1 | —CH₂CH₂CH₂CH₂— | 152–153 |
| 79 | H | H | H | H | 0 | H | H | Cl | H | 1 | —CH(CH₃)—CH(CH₃)— | 117–118 |
| 80 | H | F | H | H | 1 | H | H | Cl | H | 1 | —CH₂CH₂CH₂— | 169–170 |
| 81 | H | F | H | H | 1 | H | H | Cl | H | 1 | —CH(CH₃)—CH₂— | 108–109 |
| 82 | H | F | H | H | 1 | H | H | Cl | H | 1 | —CH₂CH₂CH₂CH₂— | 146–147 |
| 83 (*12) | H | F | H | H | 1 | H | H | Cl | H | 1 | —CH(CH₃)CH₂CH₂— | 112–113 |
| 84 | H | F | H | H | 1 | H | H | Cl | H | 1 | —CH(CH₂CH₃)—CH₂— | 112–113 |
| 85 | H | F | H | H | 1 | H | H | Cl | H | 1 | —CH₂CH₂— | 170–171 |
| 86 | H | Cl | H | H | 1 | H | H | Cl | H | 1 | —CH(CH₃)—CH(CH₃)— | 153–154 |
| 87 | H | Cl | H | H | 1 | H | H | Cl | H | 1 | —CH₂CH₂CH₂CH₂— | 142–143 |
| 88 | H | Cl | H | H | 1 | H | H | Cl | H | 1 | —CH₂CH₂— | 170–171 |
| 89 | H | Cl | H | H | 1 | H | H | Cl | H | 1 | —CH(CH₃)—CH₂— | 134–135 |
| 90 | H | Cl | H | H | 1 | H | H | Cl | H | 1 | —CH₂CH₂CH₂— | 158–159 |
| 91 | H | Cl | H | H | 1 | H | H | Cl | H | 1 | —CH(CH₂CH₃)—CH₂— | 108–109 |
| 92 (*13) | H | Cl | H | H | 1 | H | H | Cl | H | 1 | —CH(CH₃)CH₂CH₂— | 175–176 |
| 93 | H | H | H | H | 0 | H | H | H | H | 0 | —CH₂CH₂— | 134–135 |
| 94 | H | H | H | H | 0 | H | H | H | H | 0 | —CH(CH₃)—CH₂— | 131–132 |
| 95 | H | H | H | H | 0 | H | H | H | H | 0 | —CH₂CH₂CH₂— | 130–131 |
| 96 | H | H | H | H | 0 | H | H | H | H | 0 | —CH₂CH₂CH₂CH₂— | 167–168 |

TABLE 1-continued

| | | | | | | | | | | | | |
|---|---|---|---|---|---|---|---|---|---|---|---|---|
| 97 (*14) | H | H | H | H | 0 | H | H | H | H | 0 | CH₃<br>\|<br>—CHCH₂CH₂— | 147–148 |
| 98 (*15) | H | H | H | H | 0 | H | H | H | H | 0 | CH₃<br>\|<br>—CHCH₂CH₂— | 156–157 |
| 99 | H | H | H | H | 0 | H | H | H | H | 0 | CH₂CH₃<br>\|<br>—CH—CH₂— | 118–119 |
| 100 | H | H | H | H | 0 | H | H | H | H | 0 | CH₃  CH₃<br>\|     \|<br>—CH—CH— | 151–152 |
| 101 (*16) | H | F | H | H | 1 | H | H | Cl | H | 1 | CH₃<br>\|<br>—CH—CH₂CH₂— | 158–159 |
| 102 | H | F | H | H | 1 | H | H | Cl | H | 1 | CH₃  CH₃<br>\|     \|<br>—CH—CH— | 105–106 |
| 103 (*17) | H | Cl | H | H | 1 | H | H | Cl | H | 1 | CH₃<br>\|<br>—CH—CH₂—CH₂— | (*18) |
| 104 | H | H | H | H | 0 | H | H | Br | H | 1 | —CH₂—CH₂— | 117–118 |
| 105 | H | H | H | H | 0 | H | H | Br | H | 1 | CH₃<br>\|<br>—CH—CH₂— | (*19) |
| 106 | H | H | H | H | 0 | H | H | Br | H | 1 | CH₂CH₃<br>\|<br>—CH—CH₂— | (*20) |
| 107 | H | H | H | H | 0 | H | H | Br | H | 1 | —CH₂—CH₂—CH₂— | 128–129 |
| 108 | H | H | H | H | 0 | H | H | Br | H | 1 | CH₃<br>\|<br>—CH—CH₂—CH₂— | 101–102 |
| 109 | H | H | H | H | 0 | H | H | Br | H | 1 | —CH₂—CH₂CH₂CH₂— | 156–157 |
| 110 | H | H | H | H | 0 | H | H | Br | H | 1 | CH₃  CH₃<br>\|     \|<br>—CH—CH— | 148–149 |
| 111 | H | Cl | H | H | 1 | H | H | Cl | H | 1 | Bu(i) | 135–136 |
| 112 | H | Cl | H | H | 1 | H | H | H | H | 0 | Pr(i) | 134–135 |
| 113 | H | Cl | H | H | 1 | H | H | H | H | 0 | —CH₂C≡CH | 157–158 |
| 114 | H | H | H | H | 0 | H | H | Cl | H | 1 | Pr(i) | 97–98 |

(*1): NMR(CDCl₃)δ(ppm) 3.18(6H,S), 7.0–7.5(7H,m), 7.85(1H,d), 8.32(1H,d), 8,75(2H,bd), 9.50(1H,bs)
(*2): NMR(CDCl₃)δ(ppm) 3.18(6H,S), 6.91–7.72(8H,m), 8.33(1H,d, J = 9.6HZ, 4.8HZ), 8.77(2H,m), 9.41(1H,S)
(*3): NMR(CDCl₃)δ(ppm) 1.19(6H,t), 3.37(4H,q), 6.79–7.54(8H,m), 7.93–8.74(4H,m), 9.66(1H,S)
(*4): NMR(CDCl₃)δ(ppm) 1.19(6H,t), 3.37(4H,q), 7.06–7.54(8H,m), 7.93–8.74(4H,m), 9.53(1H,S)
(*5): NMR(CDCl₃)δ(ppm) 0.72–0.96(6H,m), 1.28–1.76(4H,m), 3.50–2.90(4H,m), 6.70–8.76(12H,m)
(*6): NMR(CDCl₃)δ(ppm) 2.22(3H,S), 3.15(6H,S), 6.86–7.37(6H,m), 7.45–7.55(2H,m), 7.70–7.95(1H,m), 8.34–8.50(1H,m), 8.70–8.80(2H,m), 9.76(1H,bs)
(*7): NMR(CDCl₃)δ(ppm)0.76–0.96(6H,m), 1.20–1.72(8H,m), 3.18–3.36(4H,m), 7.02–7.53(8H,m), 7.75–7.80(1H,m), 8.25–8.36(1H,m), 8.72–8.82(2H,m), 9.50(1H,bs)
(*8): NMR(CDCl₃)δ(ppm) 0.71–0.95(6H,m), 1.28–1.76(4H,m), 2.23(3H,S), 3.50–2.90(4H,m), 6.91–8.73(11H,m), 9.40(1H,S)
(*9): NMR(CDCl₃)δ(ppm) 0.97–1.30(9H,m), 2.51(2H,q), 3.36(4H,m), 6.86–8.75(12H,m), 9.60(1H,S)
(*10): NMR(CDCl₃)δ(ppm) 0.96(6H,t), 1.53(4H,m), 2.20(3H,S), 3.15(4H,t), 6.79–8.70(11H,m), 8.41(1H,S)
(*11): NMR(CDCl₃)δ(ppm) 0.80–1.12(3H,m), 1.32–2.00(2H,m), 3.40–4.42(3H,m), 7.00–7.75(9H,m), 8.21–8.41(1H,m), 8.60–8.72(2H,m), 9.68(1H,bs)
The NMR spectrum clearly states that compound No. 75 is a mixture of isomers.
(*12), (*16): Compounds No. 83 and 101 are isomers with each other.
(*13), (*17): Compounds No. 92 and 103 are isomers with each other.
(*14), (*15): Compounds No. 97 and 98 are isomers with each other.
(*18): NMR(CDCl₃)δ(ppm) 1.35(3H,d), 1.50–2.20(2H,m), 3.90–4.00(3H,m), 7.30–7.70(9H,m), 8.63–8.90(2H,m), 9.85–10.50(1H,bs)
(*19): NMR(CDCl₃)δ(ppm) 1.20–1.50(3H,m), 3.50–4.60(3H,m), 6.95–7.80(10H,m), 8.60–8.80(2H,m), 9.50–9.80(1H,bs)
The NMR spectrum clearly states that compound No. 105 is a mixture of isomers.
(*20): NMR(CDCl₃)δ(ppm) 0.75–1.20(3H,m), 1.30–2.00(2H,m), 2.10–4.50(3H,m), 7.00–7.80(9H,m), 8.20–8.50(1H,m), 8.60–8.80(2H,m), 9.50–9.80(1H,bs)

TABLE 1-continued

The NMR spectrum clearly states that compound No. 106 is a mixture of isomers.

The following comparative compounds are those described in Japanese Patent Laid Open Public No. 72825-78, which will be used hereafter in Experiments.

Comparative Compound 1

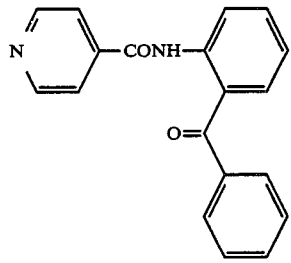

Comparative Compound 2

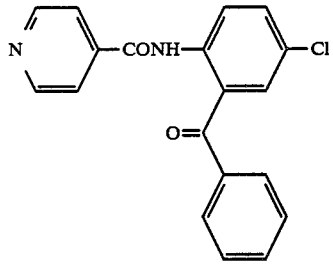

Comparative Compound 3

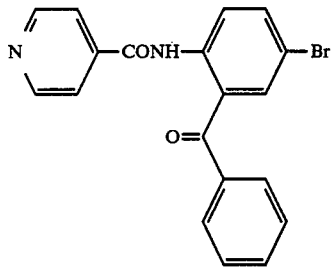

Comparative Compound 4

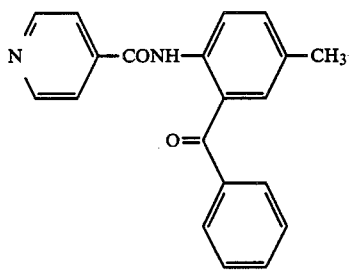

The compounds of the present invention thus prepared have systemic effects on plants, so they can be applied in various manners to treat the stem and foliage of plants over the ground, seeds, the surface of water, and the soil.

The compounds of the present invention have no adverse effects on the cultivated plants to be treated, so they can be used either before or after sowing or at any stage of the plant growth whether it is a juvenile seedling, in the midst of growth or in the fruiting stage.

The compounds of the present invention may be used alone, or in combination, without mixing with other ingredients. But in order to provide greater convenience, they may be mixed with various solid or liquid agricultural carriers so as to formulate wettable powders, emulsions, oils, dusts, granules or suspension concentrates. These formulations may be further supplemented with adjuvants such as dispersants, diluents, emulsifiers, spreaders, wetting agents, adsorbents, thickeners, anti-foaming agents and anti-freezing agents. The solids and liquid carriers may be used either alone or in combination. Illustrative carriers include talc, clay, bentonite, kaolin, diatomaceous earth, calcium carbonate, woodmeal, starch, gum arabic, water, alcohol, kerosene, naphtha, xylene, cyclohexanone, methylnaphthalene, benzene, acetone, dimethylformamide, glycol ether and N-methylpyrrolidone.

Suitable adjuvants include polyoxyethylene alkylphenyl ether, polyoxyethylene sorbitan monooleate, ethylene oxide-propylene oxide copolymer, lignin sulfonate, sorbitan esters, soaps, sulfated oils, alkyl sulfate esters, petroleum sulfonates, dioctyl sulfo-succinates, alkylbenzensulfonates, aliphatic amine salts, quaternary ammonium salts, alkyl pyridinium salts, alkylaminoethyl glycine, alkyldimethyl betaine, polyglycol sulfate esters, alkylamine sulfonic acid, isopropyl phosphate, carboxymethyl cellulose, polyvinyl alcohol, hydroxypropyl cellulose, ethylene glycol and xanthan gum.

The compounds of the present invention may also be mixed with propellants such as fluorotrichloromethane and dichlorodifluoromethane for use as aerosols. Alternatively, the compounds may be mixed with suitable foaming agents or combustion aids to prepare fumigants or formulations for smoking.

When preparing fungicides from the compounds of the present invention, they are generally used in an amount, on a weight basis, of 0.05 to 95%, preferably 0.1 to 80%, more preferably 1 to 70%, with the carriers and adjuvants being used in amounts of 70 to 99% and 0 to 20%, respectively. In order to achieve a wide spectrum of effects, the compounds may be used in combination with fertilizers or other fungicides or agrochemicals such as herbicides, plant growth regulators, insecticides and acaricides.

The concentrations of the compounds of the present invention and the relevant amounts to be applied should vary with many factors such as the season, weather, method of application, type of formulation, the location of use, the disease to be combatted and the crop plant to be treated. Generally, the concentrations of the compounds are in the range of 0.5 to 1,000 ppm, preferably 3 to 500 ppm. The amounts of the compounds applied generally range from 0.5 to 500 g, preferably from 1 to 250 g, for 10 ares.

The efficacy of the compounds of the present invention as agricultural and horticultural fungicides will become apparent by reading the following results of experiments.

EXPERIMENT 1

Test for Control on Powdery Mildew of Cucumber (Protective Effect)

A biscuit pot with a diameter of 15 cm was filled with horticultural granular soil, and ten seeds of Takasago strain cucumber were sown. After cultivation under greenhouse conditions for 10 days, the juvenile seedlings with cotyledon were tested.

These seedlings were sprayed with a dose of 15 ml per pot of a wettable powder of Formulation 2 described below which had been diluted with water at a predetermined concentration. After air drying, the seedlings were inoculated with a suspension of conidiospores of *Sphaerotheca fuliginea* by spraying it on the foliage of the seedlings. Then, the cultivation was effected at a temperature of from 23° to 26° C. for 10 days, and the seedlings were checked for the occurrence and severity of infection in terms of percent infection calculated as follows.

First, on the basis of the percentage of infected area, the test seedlings were rated on the following infection index of from 0 to 5.

| Infection index | Condition of the leaf |
| --- | --- |
| 0 | No infected area on leaf surface |
| 1 | Infected area of less than 10% on leaf surface |
| 2 | Infected area of less than 30% on leaf surface |
| 3 | Infected area of less than 60% on leaf surface |
| 4 | Infected area of less than 80% on leaf surface |
| 5 | Infected area not less than 80% on leaf surface |

Percent infection was calculated from the Infection indexes thus obtained according to the following equation:

$$\text{Percent infection} = \frac{\Sigma(\text{infection index} \times \text{number of leaves})}{5 \times (\text{total number of checked leaves})} \times 100.$$

Percent protection was obtained by comparing the percent infections (P.I.) of untreated seedlings and treated seedlings, according to the following equation:

$$\text{Percent protection} = \frac{(\text{P.I. of untreated seedlings}) - (\text{P.I. of treated seedlings})}{(\text{P.I. of untreated seedlings})} \times 100.$$

The results are shown in Table 2.

TABLE 2

| Compound No. | Concentration of the compound (ppm) | Percent infection | Percent protection | Toxicity |
| --- | --- | --- | --- | --- |
| untreated section | — | 97.85 | — | — |
| benomyl* | 150 | 9.0 | 90.8 | non |
| 1 | 150 | 0 | 100 | non |
| 2 | 150 | 0 | 100 | non |
| 3 | 150 | 0 | 100 | non |
| 4 | 150 | 0 | 100 | non |
| 6 | 150 | 0 | 100 | non |
| 7 | 150 | 0 | 100 | non |
| 8 | 150 | 0 | 100 | non |
| 9 | 150 | 0 | 100 | non |
| 13 | 150 | 0 | 100 | non |
| 14 | 150 | 0 | 100 | non |
| 15 | 150 | 0 | 100 | non |
| 16 | 150 | 0 | 100 | non |
| 17 | 150 | 0 | 100 | non |
| 18 | 150 | 0 | 100 | non |
| 21 | 150 | 0 | 100 | non |
| 22 | 150 | 0 | 100 | non |
| 23 | 150 | 0 | 100 | non |
| 24 | 150 | 0 | 100 | non |
| 25 | 150 | 0 | 100 | non |
| 30 | 150 | 0 | 100 | non |
| 41 | 150 | 0 | 100 | non |
| 42 | 150 | 0 | 100 | non |
| 44 | 150 | 0 | 100 | non |
| 46 | 150 | 0 | 100 | non |
| 47 | 150 | 0 | 100 | non |
| 49 | 150 | 0 | 100 | non |
| 50 | 150 | 0 | 100 | non |
| 51 | 150 | 0 | 100 | non |
| 52 | 150 | 0 | 100 | non |
| 54 | 150 | 0 | 100 | non |
| 55 | 150 | 0 | 100 | non |
| 57 | 150 | 0 | 100 | non |
| 59 | 150 | 0 | 100 | non |
| 63 | 150 | 0 | 100 | non |
| 67 | 150 | 0 | 100 | non |
| 68 | 150 | 0 | 100 | non |
| 69 | 150 | 0 | 100 | non |
| 71 | 150 | 0 | 100 | non |
| 73 | 150 | 0 | 100 | non |
| 74 | 150 | 0 | 100 | non |
| 75 | 150 | 0 | 100 | non |
| 76 | 150 | 0 | 100 | non |
| 79 | 150 | 0 | 100 | non |
| 80 | 150 | 0 | 100 | non |
| 84 | 150 | 0 | 100 | non |
| 85 | 150 | 0 | 100 | non |
| 86 | 150 | 0 | 100 | non |
| 88 | 150 | 0 | 100 | non |
| 92 | 150 | 0 | 100 | non |
| 95 | 150 | 0 | 100 | non |
| 96 | 150 | 0 | 100 | non |
| 97 | 150 | 0 | 100 | non |
| 98 | 150 | 0 | 100 | non |
| 101 | 150 | 0 | 100 | non |
| 103 | 150 | 0 | 100 | non |
| 104 | 150 | 0 | 100 | non |
| 106 | 150 | 0 | 100 | non |
| 107 | 150 | 0 | 100 | non |
| 108 | 150 | 0 | 100 | non |
| 109 | 150 | 0 | 100 | non |
| 110 | 150 | 0 | 100 | non |
| 111 | 150 | 0 | 100 | non |
| Comparative Compound 2 | 150 | 14.0 | 85.7 | non |
| Comparative Compound 3 | 150 | 13.0 | 86.7 | non |

*benomyl: Methyl 1-(butylcarbamoyl)-2-benzimidazolcarbamate

EXPERIMENT 2

Test for Control on Powdery Mildew of Cucumber (Curative Effect)

A biscuit pot with a diameter of 15 cm was filled with horticultural granular soil, and ten seeds of Takasago strain cucumber were sown. After cultivation under greenhouse conditions for 10 days, the juvenile seedlings with completely developed cotyledon were tested.

The seedlings were inoculated with a suspension of conidiospores of *Sphaerotheca fuliginea* by spraying, and after leaving at a temperature of from 23° to 26° C. for one day, were sprayed with a dose of 15 ml per pot of an emulsion prepared from Formulation 5 described below by dilution with water at a predetermined concentration. After air drying, the seedlings were cultivated at 23°–26° C. under greenhouse conditions for 10 days, and checked for the occurrence and severity of infection.

Infection index, percent infection and percent protection on this experiment were determined as in Experiment 1.

The results are shown in Table 3 below.

TABLE 3

| Compound No. | Concentration of the compound (ppm) | Percent infection | Percent protection | Toxicity |
| --- | --- | --- | --- | --- |
| untreated section | — | 95.4 | — | — |
| benomyl | 150 | 15.0 | 84.3 | non |
| 1 | 150 | 0 | 100 | non |
| 2 | 150 | 0 | 100 | non |
| 3 | 150 | 0 | 100 | non |
| 4 | 150 | 0 | 100 | non |
| 6 | 150 | 0 | 100 | non |
| 7 | 150 | 0 | 100 | non |
| 8 | 150 | 0 | 100 | non |
| 9 | 150 | 0 | 100 | non |
| 13 | 150 | 0 | 100 | non |
| 14 | 150 | 0 | 100 | non |
| 15 | 150 | 0 | 100 | non |
| 16 | 150 | 0 | 100 | non |
| 17 | 150 | 0 | 100 | non |
| 18 | 150 | 0 | 100 | non |
| 21 | 150 | 0 | 100 | non |
| 22 | 150 | 0 | 100 | non |
| 23 | 150 | 0 | 100 | non |
| 24 | 150 | 0 | 100 | non |
| 25 | 150 | 0 | 100 | non |
| 30 | 150 | 0 | 100 | non |
| 41 | 150 | 0 | 100 | non |
| 42 | 150 | 0 | 100 | non |
| 44 | 150 | 0 | 100 | non |
| 46 | 150 | 0 | 100 | non |
| 48 | 150 | 0 | 100 | non |
| 49 | 150 | 0 | 100 | non |
| 51 | 150 | 0 | 100 | non |
| 52 | 150 | 0 | 100 | non |
| 53 | 150 | 0 | 100 | non |
| 54 | 150 | 0 | 100 | non |
| 55 | 150 | 0 | 100 | non |
| 56 | 150 | 0 | 100 | non |
| 58 | 150 | 0 | 100 | non |
| 59 | 150 | 0 | 100 | non |
| 60 | 150 | 0 | 100 | non |
| 61 | 150 | 0 | 100 | non |
| 62 | 150 | 0 | 100 | non |
| 65 | 150 | 0 | 100 | non |
| 72 | 150 | 0 | 100 | non |
| 73 | 150 | 0 | 100 | non |
| 74 | 150 | 0 | 100 | non |
| 75 | 150 | 0 | 100 | non |
| 76 | 150 | 0 | 100 | non |
| 77 | 150 | 0 | 100 | non |
| 78 | 150 | 0 | 100 | non |
| 81 | 150 | 0 | 100 | non |
| 83 | 150 | 0 | 100 | non |
| 87 | 150 | 0 | 100 | non |
| 90 | 150 | 0 | 100 | non |
| 93 | 150 | 0 | 100 | non |
| 94 | 150 | 0 | 100 | non |
| 97 | 150 | 0 | 100 | non |
| 98 | 150 | 0 | 100 | non |
| 100 | 150 | 0 | 100 | non |
| 102 | 150 | 0 | 100 | non |
| 105 | 150 | 0 | 100 | non |
| 111 | 150 | 0 | 100 | non |
| Comparative Compound 1 | 150 | 20.0 | 79 | non |
| Comparative Compound 3 | 150 | 21.0 | 78 | non |

EXPERIMENT 3

Test for Control on Powdery Mildew of Wheat (Protective Effect)

A biscuit pot with a diameter of 12 cm was filled with horticultural granular soil known by the name of "Arakida" and 15 grains of wheat (Norin No. 61 strain) were seeded. After cultivation under greenhouse conditions for 12 days, the juvenile seedlings at the one-leaf stage were subjected to the following test.

These seedlings were sprayed with a dose of 15 ml per pot of wettable powder of Formulation 6 described below which had been diluted with water at a predetermined concentration. After air drying, the seedlings were inoculated with a suspension of conidiospores of *Erysiphe graminis*, and after cultivation at a temperature of from 20° to 24° C. under greenhouse conditions for 10 days, were checked for the occurrence and severity of infection.

Infection index, percent infection and percent protection were determined as in Experiment 1.

The results are shown in Table 4 below.

TABLE 4

| Compound No. | Concentration of the compound (ppm) | Percent infection | Percent protection | Toxicity |
| --- | --- | --- | --- | --- |
| untreated section | — | 85.0 | — | — |
| Thiophanate methyl* | 150 | 8.0 | 90.6 | non |
| 1 | 150 | 0 | 100 | non |
| 2 | 150 | 0 | 100 | non |
| 3 | 150 | 0 | 100 | non |
| 4 | 150 | 0 | 100 | non |
| 6 | 150 | 0 | 100 | non |
| 7 | 150 | 0 | 100 | non |
| 8 | 150 | 0 | 100 | non |
| 9 | 150 | 0 | 100 | non |
| 10 | 150 | 0 | 100 | non |
| 13 | 150 | 0 | 100 | non |
| 14 | 150 | 0 | 100 | non |
| 15 | 150 | 0 | 100 | non |
| 16 | 150 | 0 | 100 | non |
| 17 | 150 | 0 | 100 | non |
| 18 | 150 | 0 | 100 | non |
| 22 | 150 | 0 | 100 | non |
| 23 | 150 | 0 | 100 | non |
| 24 | 150 | 0 | 100 | non |
| 25 | 150 | 0 | 100 | non |
| 30 | 150 | 0 | 100 | non |
| 41 | 150 | 0 | 100 | non |
| 42 | 150 | 0 | 100 | non |
| 44 | 150 | 0 | 100 | non |
| 46 | 150 | 0 | 100 | non |
| 49 | 150 | 0 | 100 | non |
| 51 | 150 | 0 | 100 | non |
| 52 | 150 | 0 | 100 | non |
| 53 | 150 | 0 | 100 | non |
| 54 | 150 | 0 | 100 | non |
| 55 | 150 | 0 | 100 | non |
| 59 | 150 | 0 | 100 | non |
| 64 | 150 | 0 | 100 | non |
| 73 | 150 | 0 | 100 | non |
| 74 | 150 | 0 | 100 | non |
| 75 | 150 | 0 | 100 | non |
| 76 | 150 | 0 | 100 | non |
| 82 | 150 | 0 | 100 | non |
| 89 | 150 | 0 | 100 | non |
| 99 | 150 | 0 | 100 | non |
| 104 | 150 | 0 | 100 | non |
| 105 | 150 | 0 | 100 | non |
| 107 | 150 | 0 | 100 | non |
| Comparative | 150 | 11.0 | 87 | non |

TABLE 4-continued

| Compound No. | Concentration of the compound (ppm) | Percent infection | Percent protection | Toxicity |
|---|---|---|---|---|
| Compound 2 | | | | |

*thiophanate methyl: Dimethyl 4,4'-O—phenylenebis (3-thioallophanate)

EXPERIMENT 4

Test for Control of Powdery Mildew of Wheat (Curative Effect)

A biscuit pot with a diameter of 12 cm was filled with horticultural granular soil known by the name of "Arakida", and 15 grains of wheat (Norin No. 61 strain) were seeded. Then cultivation was effected under greenhouse conditions for 12 days and the juvenile seedlings at the one-leaf stage were used for the following tests.

These seedlings were inoculated by spraying with a suspension of conidiospores of *Erysiphe graminis,* and after allowing to stand for one day at 20°-23° C. under greenhouse conditions, were sprayed with a dose of 15 ml of wettable powder of Formulation 2 described below which had been diluted with water at a predetermined concentration. After air drying, the seedlings were cultivated at 20°-24° C. under greenhouse conditions for 10 days and checked for the occurrence and severity of infection.

Infection index, percent infection and percent protection were determined as in Experiment 1.

The results are shown in Table 5 below.

TABLE 5

| Compound No. | Concentration of the compound (ppm) | Percent infection | Percent protection | Toxicity |
|---|---|---|---|---|
| untreated section | — | 83.5 | — | — |
| Thiophanate methyl | 150 | 15.0 | 82.0 | non |
| 1 | 150 | 0 | 100 | non |
| 2 | 150 | 0 | 100 | non |
| 3 | 150 | 0 | 100 | non |
| 4 | 150 | 0 | 100 | non |
| 6 | 150 | 0 | 100 | non |
| 7 | 150 | 0 | 100 | non |
| 8 | 150 | 0 | 100 | non |
| 9 | 150 | 0 | 100 | non |
| 10 | 150 | 0 | 100 | non |
| 13 | 150 | 0 | 100 | non |
| 14 | 150 | 0 | 100 | non |
| 15 | 150 | 0 | 100 | non |
| 16 | 150 | 0 | 100 | non |
| 17 | 150 | 0 | 100 | non |
| 18 | 150 | 0 | 100 | non |
| 22 | 150 | 0 | 100 | non |
| 23 | 150 | 0 | 100 | non |
| 24 | 150 | 0 | 100 | non |
| 25 | 150 | 0 | 100 | non |
| 30 | 150 | 0 | 100 | non |
| 41 | 150 | 0 | 100 | non |
| 44 | 150 | 0 | 100 | non |
| 46 | 150 | 0 | 100 | non |
| 49 | 150 | 0 | 100 | non |
| 51 | 150 | 0 | 100 | non |
| 54 | 150 | 0 | 100 | non |
| 55 | 150 | 0 | 100 | non |
| 59 | 150 | 0 | 100 | non |
| 66 | 150 | 0 | 100 | non |
| 73 | 150 | 0 | 100 | non |
| 74 | 150 | 0 | 100 | non |
| 76 | 150 | 0 | 100 | non |
| 91 | 150 | 0 | 100 | non |

TABLE 5-continued

| Compound No. | Concentration of the compound (ppm) | Percent infection | Percent protection | Toxicity |
|---|---|---|---|---|
| 101 | 150 | 0 | 100 | non |
| 103 | 150 | 0 | 100 | non |
| 104 | 150 | 0 | 100 | non |
| 105 | 150 | 0 | 100 | non |
| 107 | 150 | 0 | 100 | non |
| Comparative Compound 3 | 150 | 17.0 | 79.6 | non |
| Comparative Compound 4 | 150 | 15.0 | 82.0 | non |

EXPERIMENT 5

Test for Control on Powdery Mildew of Cucumber (Protective Effect)

Tests similar to those of Experiment 1 were conducted except for using a smaller dose of the active compound as shown.

The results are given in Table 6.

TABLE 6

| Compound No. | Concentration of the compound (ppm) | Percent infection | Percent protection | Toxicity |
|---|---|---|---|---|
| untreated section | — | 100 | — | — |
| 9 | 100 | 0 | 100 | non |
|  | 6.2 | 0 | 100 | non |
| 13 | 100 | 0 | 100 | non |
|  | 6.2 | 0 | 100 | non |
| 16 | 100 | 0 | 100 | non |
|  | 6.2 | 0 | 100 | non |
| 23 | 100 | 0 | 100 | non |
|  | 6.2 | 0 | 100 | non |
| 30 | 100 | 0 | 100 | non |
|  | 6.2 | 0 | 100 | non |
| 42 | 100 | 0 | 100 | non |
|  | 6.2 | 0 | 100 | non |
| 43 | 100 | 0 | 100 | non |
|  | 6.2 | 0 | 100 | non |
| 44 | 100 | 0 | 100 | non |
|  | 6.2 | 0 | 100 | non |
| 46 | 100 | 0 | 100 | non |
|  | 6.2 | 0 | 100 | non |
| 49 | 100 | 0 | 100 | non |
|  | 6.2 | 0 | 100 | non |
| 51 | 100 | 0 | 100 | non |
|  | 6.2 | 0 | 100 | non |
| 52 | 100 | 0 | 100 | non |
|  | 6.2 | 0 | 100 | non |
| 55 | 100 | 0 | 100 | non |
|  | 6.2 | 0 | 100 | non |
| 59 | 100 | 0 | 100 | non |
|  | 6.2 | 0 | 100 | non |
| 63 | 100 | 0 | 100 | non |
|  | 6.2 | 0 | 100 | non |
| 66 | 100 | 0 | 100 | non |
|  | 6.2 | 0 | 100 | non |
| 77 | 100 | 0 | 100 | non |
|  | 6.2 | 0 | 100 | non |
| 78 | 100 | 0 | 100 | non |
|  | 6.2 | 0 | 100 | non |
| 79 | 100 | 0 | 100 | non |
|  | 6.2 | 0 | 100 | non |
| 82 | 100 | 0 | 100 | non |
|  | 6.2 | 0 | 100 | non |
| 83 | 100 | 0 | 100 | non |
|  | 6.2 | 0 | 100 | non |
| 84 | 100 | 0 | 100 | non |
|  | 6.2 | 0 | 100 | non |
| 85 | 100 | 0 | 100 | non |
|  | 6.2 | 0 | 100 | non |
| 86 | 100 | 0 | 100 | non |
|  | 6.2 | 0 | 100 | non |

TABLE 6-continued

| Compound No. | Concentration of the compound (ppm) | Percent infection | Percent protection | Toxicity |
|---|---|---|---|---|
| 87 | 100 | 0 | 100 | non |
|  | 6.2 | 0 | 100 | non |
| 88 | 100 | 0 | 100 | non |
|  | 6.2 | 0 | 100 | non |
| 89 | 100 | 0 | 100 | non |
|  | 6.2 | 0 | 100 | non |
| 90 | 100 | 0 | 100 | non |
|  | 6.2 | 0 | 100 | non |
| 91 | 100 | 0 | 100 | non |
|  | 6.2 | 0 | 100 | non |
| 102 | 100 | 0 | 100 | non |
|  | 6.2 | 0 | 100 | non |
| 103 | 100 | 0 | 100 | non |
|  | 6.2 | 0 | 100 | non |
| 104 | 100 | 0 | 100 | non |
|  | 6.2 | 0 | 100 | non |
| 105 | 100 | 0 | 100 | non |
|  | 6.2 | 0 | 100 | non |
| 106 | 100 | 0 | 100 | non |
|  | 6.2 | 0 | 100 | non |
| 107 | 100 | 0 | 100 | non |
|  | 6.2 | 0 | 100 | non |
| 108 | 100 | 0 | 100 | non |
|  | 6.2 | 0 | 100 | non |

EXPERIMENT 6

Test for Control on Powdery Mildew of Cucumber (Curative Effect)

Tests similar to those in Experiment 2 were conducted except for using a smaller dose of the active compound as indicated below.

The results are shown in Table 7.

TABLE 7

| Compound No. | Concentration of the compound (ppm) | Percent infection | Percent protection | Toxicity |
|---|---|---|---|---|
| untreated section | — | 100 | 0 | — |
| 4 | 100 | 0 | 100 | non |
|  | 6.2 | 0 | 100 | non |
| 9 | 100 | 0 | 100 | non |
|  | 6.2 | 0 | 100 | non |
| 16 | 100 | 0 | 100 | non |
|  | 6.2 | 0 | 100 | non |
| 22 | 100 | 0 | 100 | non |
|  | 6.2 | 0 | 100 | non |
| 23 | 100 | 0 | 100 | non |
|  | 6.2 | 0 | 100 | non |
| 25 | 100 | 0 | 100 | non |
|  | 6.2 | 0 | 100 | non |
| 33 | 100 | 0 | 100 | non |
|  | 6.2 | 0 | 100 | non |
| 42 | 100 | 0 | 100 | non |
|  | 6.2 | 0 | 100 | non |
| 44 | 100 | 0 | 100 | non |
|  | 6.2 | 0 | 100 | non |
| 46 | 100 | 0 | 100 | non |
|  | 6.2 | 0 | 100 | non |
| 47 | 100 | 0 | 100 | non |
|  | 6.2 | 0 | 100 | non |
| 49 | 100 | 0 | 100 | non |
|  | 6.2 | 0 | 100 | non |
| 51 | 100 | 0 | 100 | non |
|  | 6.2 | 0 | 100 | non |
| 52 | 100 | 0 | 100 | non |
|  | 6.2 | 0 | 100 | non |
| 54 | 100 | 0 | 100 | non |
|  | 6.2 | 0 | 100 | non |
| 55 | 100 | 0 | 100 | non |
|  | 6.2 | 0 | 100 | non |
| 62 | 100 | 0 | 100 | non |

TABLE 7-continued

| Compound No. | Concentration of the compound (ppm) | Percent infection | Percent protection | Toxicity |
|---|---|---|---|---|
|  | 6.2 | 0 | 100 | non |
| 66 | 100 | 0 | 100 | non |
|  | 6.2 | 0 | 100 | non |
| 68 | 100 | 0 | 100 | non |
|  | 6.2 | 0 | 100 | non |
| 72 | 100 | 0 | 100 | non |
|  | 6.2 | 0 | 100 | non |
| 77 | 100 | 0 | 100 | non |
|  | 6.2 | 0 | 100 | non |
| 79 | 100 | 0 | 100 | non |
|  | 6.2 | 0 | 100 | non |
| 80 | 100 | 0 | 100 | non |
|  | 6.2 | 0 | 100 | non |
| 81 | 100 | 0 | 100 | non |
|  | 6.2 | 0 | 100 | non |
| 83 | 100 | 0 | 100 | non |
|  | 6.2 | 0 | 100 | non |
| 85 | 100 | 0 | 100 | non |
|  | 6.2 | 0 | 100 | non |
| 89 | 100 | 0 | 100 | non |
|  | 6.2 | 0 | 100 | non |
| 92 | 100 | 0 | 100 | non |
|  | 6.2 | 0 | 100 | non |
| 103 | 100 | 0 | 100 | non |
|  | 6.2 | 0 | 100 | non |
| 104 | 100 | 0 | 100 | non |
|  | 6.2 | 0 | 100 | non |
| 105 | 100 | 0 | 100 | non |
|  | 6.2 | 0 | 100 | non |
| 106 | 100 | 0 | 100 | non |
|  | 6.2 | 0 | 100 | non |
| 107 | 100 | 0 | 100 | non |
|  | 6.2 | 0 | 100 | non |
| 108 | 100 | 0 | 100 | non |
|  | 6.2 | 0 | 100 | non |

EXPERIMENT 7

Test for Control on Downy Mildew of Cucumber (Protective Effect)

A biscuit pot with a diameter of 12 cm was filled with commercial horticultural soil (Kureha Kagaku, Tokyo, Japan), ten seeds of cucumber (Ochiai-aonagafushinari strain) were sown and cultivated under greenhouse conditions for 10 days. The juvenile seedlings with cotyledon were sprayed with an emulsifiable concentrate of the compound of this invention which had been diluted with water at a predetermined concentration so that the surface of leaves are fully wetted with the sprayed emulsion of Formulation 7. Then, the seedlings were cultivated under greenhouse conditions for two days, and inoculated with a suspension of conidiospores of *Pseudoperonospora cubensis* by spraying it as an aqueous suspension. The treated seedlings were allowed to stand at 21°–22° C. in a humid atmosphere for 3 days, cultivated at 21°–22° C. under the light of fluorescent lamps, and checked for the occurrence and severity of infection in terms of percent infection calculated as follows.

First, on the basis of the percentage of infected area, the test seedlings were rated on the infection index of from 0 to 5.

| Infection index | Condition of the leaf |
|---|---|
| 0 | No infected area on leaf surface |
| 1 | Infected area of less than 10% on leaf surface |
| 2 | Infected area of less than 30% on leaf surface |

-continued

| Infection index | Condition of the leaf |
|---|---|
| 3 | Infected area of less than 60% on leaf surface |
| 4 | Infected area of less than 80% on leaf surface |
| 5 | Infected area not less than 80% on leaf surface |

Second, on the basis of the infection indexes, percent infection was calculated by the following equation:

Percent infection =

$$\frac{\Sigma(\text{infection index} \times \text{number of leaves})}{(\text{total number of checked leaves}) \times 5} \times 100.$$

Then, percent protection was calculated on the basis of the equation below.

Percent protection =

$$\frac{(\text{percent infection in untreated seedlings}) - (\text{percent infection in treated seedlings})}{(\text{percent infection in untreated seedlings})} \times 100.$$

The results are shown in Table 8.

TABLE 8

| Compound No. | Concentration of the compound (ppm) | Percent infection | Percent protection | Toxicity |
|---|---|---|---|---|
| untreated section | — | 100 | — | — |
| *TPN | 250 | 85 | 15 | non |
| 9 | 250 | 0 | 100 | non |
| 13 | 250 | 0 | 100 | non |
| 16 | 250 | 0 | 100 | non |
| 23 | 250 | 0 | 100 | non |
| 25 | 250 | 0 | 100 | non |
| 27 | 250 | 0 | 100 | non |
| 42 | 250 | 0 | 100 | non |
| 43 | 250 | 0 | 100 | non |
| 73 | 250 | 0 | 100 | non |
| 74 | 250 | 0 | 100 | non |
| 85 | 250 | 0 | 100 | non |
| 88 | 250 | 0 | 100 | non |
| 89 | 250 | 0 | 100 | non |
| 92 | 250 | 0 | 100 | non |
| 104 | 250 | 0 | 100 | non |

*TPN: tetrachlorisophthalonitrile

EXPERIMENT 8

Test for Control on Damping-Off Disease of Cucumber Seedling

A Neubauer pot was filled with field soil, and pathogenic soil in which *Pythium aphanidernatum* had been cultivated was blended with the field soil in a layer of a depth of 2 cm in the pot to inoculate the soil with the pathogenic fungus. The pot was allowed to stand at 28° C. under super humid conditions for 24 hours in a greenhouse, and subjected to soil injection treatment at a predetermined dose level with wettable powder of Formulation 4 described below which has been diluted with water. Ten seeds of cucumber (Ochiai-aonagafu-shinari strain) were sown and lightly covered with the same field soil. After two week cultivation under greenhouse conditions, the seedlings were checked for the occurrence of infection, and the good seedling rate was calculated by the following equation:

Good seedling rate (%) =

$$\frac{\text{number of good seedlings in test section}}{\text{number of seedlings germinating in untreated and non-inoculated section}} \times 100.$$

The results are shown in Table 9 below.

TABLE 9

| Compound No. | Concentration of the compound (mg/pot) | Good seadling rate (%) |
|---|---|---|
| untreated section | — | 0 |
| *hymexazole | 20 | 60 |
| 9 | 20 | 100 |
| 13 | 20 | 100 |
| 16 | 20 | 100 |
| 23 | 20 | 100 |
| 42 | 20 | 100 |
| 44 | 20 | 100 |
| 73 | 20 | 100 |
| 77 | 20 | 100 |
| 79 | 20 | 100 |
| 85 | 20 | 100 |
| 88 | 20 | 100 |
| 89 | 20 | 100 |
| 91 | 20 | 100 |
| 93 | 20 | 100 |
| 103 | 20 | 100 |
| 104 | 20 | 100 |
| 108 | 20 | 100 |

*hymexazole: 3-Hydroxy-5-methylisoxazole

This invention is further illustrated by the following formulation examples. It should be understood that the active compounds, carriers, adjuvants and the mixing proportions of the formulation of this invention are not limited to the following formulations. Incidentally, all parts in the formulation examples are by weight.

FORMULATION 1: DUST

| Compound No. 4 | 2 parts |
|---|---|
| Clay | 98 parts |

The components above were thoroughly mixed and finely divided to give dust.

FORMULATION 2: WETTABLE POWDER

| Compound No. 7 | 10 parts |
|---|---|
| Sodium alkylsulfonate | 5 parts |
| Clay | 85 parts |

All the components above were thoroughly mixed and finely divided to give wettable powder.

FORMULATION 3: WETTABLE POWDER

| Compound No. 30 | 10 parts |
|---|---|
| Sodium alkylsulfonate | 5 parts |
| Clay | 85 parts |

All the components were thoroughly mixed and finely pulverized to give wettable powder.

FORMULATION 4: WETTABLE POWDER

| Compound No. 74 | 10 parts |
|---|---|
| Sodium alkylsulfonate | 5 parts |

| | |
|---|---|
| -continued | |
| Clay | 85 parts |

All the components were thoroughly mixed and finely pulverized to give wettable powder.

FORMULATION 5: EMULSIFIABLE CONCENTRATE

| | |
|---|---|
| Compound No. 9 | 5 parts |
| Calcium alkylbenzenesulfonate | 4 parts |
| Polyoxyethylene alkylphenyl ether | 11 parts |
| Cyclohexanone | 10 parts |
| Xylene | 70 parts |

All the components were mixed uniformly to give an emulsifiable concentrate. For use, this emulsifiable concentrate is diluted with water to a desired level and sprayed.

FORMULATION 6: EMULSIFIABLE CONCENTRATE

| | |
|---|---|
| Compound No. 44 | 5 parts |
| Calcium alkylbenzene sulfonate | 4 parts |
| Polyoxyethylene alkylphenyl ether | 11 parts |
| Cyclohexanone | 10 parts |
| Xylene | 70 parts |

All the components were mixed uniformly to give an emulsifiable concentrate.

FORMULATION 7: EMULSIFIABLE CONCENTRATE

| | |
|---|---|
| Compound No. 81 | 5 parts |
| Calcium alkylbenzene sulfonate | 4 parts |
| Polyoxyethylene alkylphenyl ether | 11 parts |
| Cyclohexanone | 10 parts |
| Xylene | 70 parts |

All the components were mixed uniformly to give an emulsifiable concentrate.

FORMULATION 8: EMULSIFIABLE CONCENTRATE

| | |
|---|---|
| Compound No. 16 | 10 parts |
| Calcium alkylbenzene sulfonate | 3 parts |
| Polyoxyethylene alkylphenyl ether | 12 parts |
| Dimethylformamide | 10 parts |
| Xylene | 65 parts |

All the components were mixed uniformly to give an emulsifiable concentrate.

FORMULATION 9: GRANULES

| | |
|---|---|
| Compound No. 22 | 2 parts |
| Calcium lignin sulfonate | 2 parts |
| Bentonite | 30 parts |
| Talc | 66 parts |

All the components were mixed uniformly. Water was added to the mixture and kneaded, granulated, and dried to give granules.

FORMULATION 10: SUSPENSION CONCENTRATE

| | |
|---|---|
| Compound No. 14 | 10 parts |
| Ethylene glycol | 5 parts |
| Xanthan gum | 0.2 parts |
| Polyoxyethylene sorbitan mono-oleate | 5 parts |
| Water | 79.8 parts |

All the components were mixed and wet-pluverized to give a suspension concentrate.

What is claimed is:

1. A ketal compound of the formula:

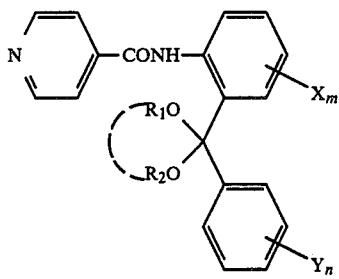

wherein X is a halogen atom, a trifluoromethyl group or a lower alkyl group; Y is a halogen atom, a lower alkyl group or a lower alkyloxy group; m and n each independently are an integer of 0 to 2, and when m or n is 2, the plurality of each of X or Y may have the same or different meanings; $R_1$ and $R_2$ independently represent a lower alkyl, allyl or propargyl group, or $R_1$ and $R_2$ together form a branched or unbranched lower alkylene chain which, when taken together with

to which they are attached, form a ring structure.

2. A ketal compound according to claim 1 wherein X is a halogen atom.

3. A ketal compound according to claim 1 wherein X is a trifluoromethyl group.

4. A ketal compound according to claim 1 wherein X is a lower alkyl group.

5. A ketal compound according to claim 1 wherein Y is a halogen atom.

6. A ketal compound according to claim 1 wherein Y is a lower alkyl group.

7. A ketal compound according to claim 1 wherein Y is a lower alkyloxy group.

8. A ketal compound according to claim 1 wherein $R_1$ and $R_2$ independently represent a lower alkyl group.

9. A ketal compound according to claim 1 wherein $R_1$ and $R_2$ independently represent an allyl group or a propargyl group.

10. A ketal compound according to claim 1 wherein $R_1$ and $R_2$ together form a branched or unbranched alkylene chain which, when taken together with

to which they are attached, form a ring structure.

11. A ketal compound according to claim 1 wherein $R_1$ and $R_2$ together are a branched alkylene group which, when taken together with

to which they are attached, form a ring structure.

12. A ketal compound according to claim 1 wherein m is 0, Y is a 4-halogen atom, and $R_1$ and $R_2$ independently represent a lower alkyl group.

13. A ketal compound according to claim 1 wherein m is 0, Y is a chlorine or bromine atom at 4-position, and $R_1$ and $R_2$ are each an ethyl group.

14. An agricultural and horticultural fungicide, particularly effective against powdery mildew, consisting essentially of an effective amount of a combination of at least two different ketal compounds of the formula:

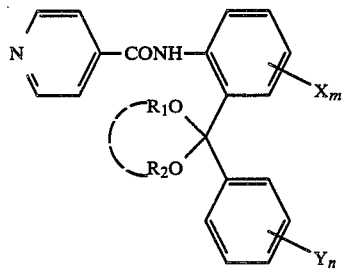

wherein X is a halogen atom, a trifluoromethyl group or a lower alkyl group; Y is a halogen atom, a lower alkyl group or a lower alkyloxy group; m and n each independently are an integer of 0 to 2, and when m or n is 2, the plurality of each of X and Y may have the same or different meanings; $R_1$ and $R_2$ independent represent a lower alkyl, allyl or propargyl group, or $R_1$ and $R_2$ together form a branched or unbranched lower alkylene chain which, when taken together with

to which they are attached, form a ring structure.

15. An agricultural and horticultural fungicide composition, particularly effective against powdery mildew, comprising an effective amount of a ketal compound of the following formula, together with a solid or liquid carrier, and an optional adjuvant:

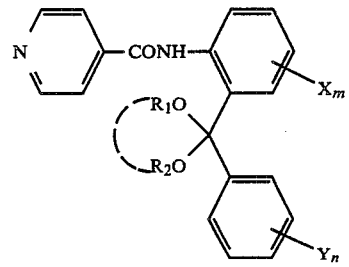

wherein X is a halogen atom, a trifluoromethyl group or a lower alkyl group; Y is a halogen atom, a lower alkyl group or a lower alkyloxy group; m and n each independently are an integer of 0 to 2, and when m or n is 2, the plurality of each of X and Y may have the same or different meanings; $R_1$ and $R_2$ independent represent a lower alkyl, allyl or propargyl group, or $R_1$ and $R_2$ together form a branched or unbranched lower alkylene chain which, when taken together with

to which they are attached, form a ring structure.

16. A fungicide according to claim 15 which is formulated as a wettable powder, an emulsion, an oil, a dust, a granule or a suspension concentrate.

17. A composition according to claim 15 which comprises 0.05 to 95% by weight of said compound, together with 70 to 99% by weight of the carrier and 0 to 20% by weight of the adjuvant.

18. A composition according to claim 15 which comprises 0.1 to 80% by weight of said compound, together with 70 to 99% by weight of the carrier and 0 to 20% by weight of the adjuvant.

19. A composition according to claim 15 which comprises 1 to 70% by weight of said compound, together with 70 to 99% by weight of the carrier and 0 to 20% by weight of the adjuvant.

20. A method of controlling powdery mildew in plants or on soil by applying an effective amount of a ketal compound of the following formula to the plant or the location:

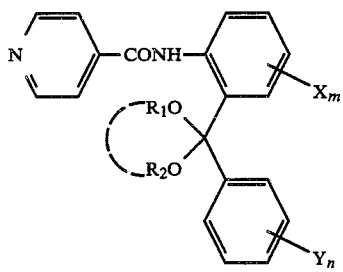

wherein X is a halogen atom, a trifluoromethyl group or a lower alkyl group; Y is a halogen atom, a lower alkyl group or a lower alkyloxy group; m and n each independently are an integer of 0 to 2, and when m or n is 2, the plurality of each of X and Y may have the same or different meanings; $R_1$ and $R_2$ independent represent a lower alkyl, allyl or propargyl group, or $R_1$ and $R_2$ together form a branched or unbranched lower alkylene chain which, when taken together with
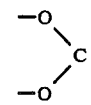
to which they are attached, form a ring structure.
21. A method according to claim 20 wherein said compound is used in an amount of 0.5 to 500 g for 10 ares.
22. A method according to claim 20 wherein said compound is used in an amount of 1 to 250 g for 10 ares.
* * * * *